(12) United States Patent
Ju et al.

(10) Patent No.: US 11,571,223 B2
(45) Date of Patent: Feb. 7, 2023

(54) DEVICE AND METHOD FOR CUTTING INTO A CANCELLOUS BONE

(71) Applicant: JOY MEDICAL DEVICES CORPORATION, Kaohsiung (TW)

(72) Inventors: Chien-Ping Ju, Kansas City, MO (US); Jiin-Huey Chern Lin, Winnetka, IL (US); Yen-Chun Chen, Kaohsiung (TW); Bing-Chen Yang, Kaohsiung (TW); Guan-Ting Chen, Tainan (TW)

(73) Assignee: JOY MEDICAL DEVICES CORPORATION, Kaohsiung (TW)

( * ) Notice: Subject to any disclaimer, the term of this patent is extended or adjusted under 35 U.S.C. 154(b) by 381 days.

(21) Appl. No.: 16/649,418

(22) PCT Filed: Oct. 17, 2018

(86) PCT No.: PCT/US2018/056188
§ 371 (c)(1),
(2) Date: Mar. 20, 2020

(87) PCT Pub. No.: WO2019/083784
PCT Pub. Date: May 2, 2019

(65) Prior Publication Data
US 2020/0297359 A1    Sep. 24, 2020

Related U.S. Application Data

(60) Provisional application No. 62/577,219, filed on Oct. 26, 2017.

(51) Int. Cl.
*A61B 17/16* (2006.01)

(52) U.S. Cl.
CPC ...... *A61B 17/1697* (2013.01); *A61B 17/1615* (2013.01); *A61B 17/1631* (2013.01)

(58) Field of Classification Search
CPC ............ A61B 17/1631; A61B 17/1633; A61B 17/164; A61B 17/1697; A61B 17/1615
See application file for complete search history.

(56) References Cited

U.S. PATENT DOCUMENTS

| | | | | |
|---|---|---|---|---|
| 1,685,380 A | * | 9/1928 | Shultz | B25B 27/00 15/93.1 |
| 5,275,610 A | * | 1/1994 | Eberbach | A61B 17/0218 606/198 |
| 5,678,572 A | * | 10/1997 | Shaw | A61B 17/0218 606/198 |
| 5,833,628 A | * | 11/1998 | Yuan | A61B 17/1664 606/180 |
| 2003/0208219 A1 | | 11/2003 | Aznoian et al. | |
| 2005/0182417 A1 | * | 8/2005 | Pagano | A61B 17/8811 606/92 |

(Continued)

FOREIGN PATENT DOCUMENTS

CN     104546085 A     4/2015

*Primary Examiner* — Matthew J Lawson
(74) *Attorney, Agent, or Firm* — Bacon & Thomas, PLLC

(57) ABSTRACT

A wire cutter suitable for creating a cavity in cancellous bone includes a restrainer and a cutting wire, wherein a portion of the cutting wire will protrude from a slot formed on the restrainer to the outside of the restrainer and inside a bone, when the cutting wire is advanced in a tunnel formed in the restrainer and toward a closed end of the tunnel.

20 Claims, 17 Drawing Sheets

(56) References Cited

U.S. PATENT DOCUMENTS

| | | | |
|---|---|---|---|
| 2008/0221608 A1* | 9/2008 | Betts | A61B 17/8825 606/191 |
| 2008/0300636 A1* | 12/2008 | Carli | A61B 17/8858 606/280 |
| 2010/0076503 A1 | 3/2010 | Beyar et al. | |
| 2010/0174286 A1 | 7/2010 | Truckai et al. | |
| 2013/0018385 A1 | 1/2013 | Keene et al. | |
| 2013/0030456 A1* | 1/2013 | Assell | A61B 17/7055 606/170 |
| 2013/0165935 A1* | 6/2013 | Griffiths | A61B 17/1617 606/80 |
| 2022/0071770 A1* | 3/2022 | Assell | A61B 17/320016 |

* cited by examiner

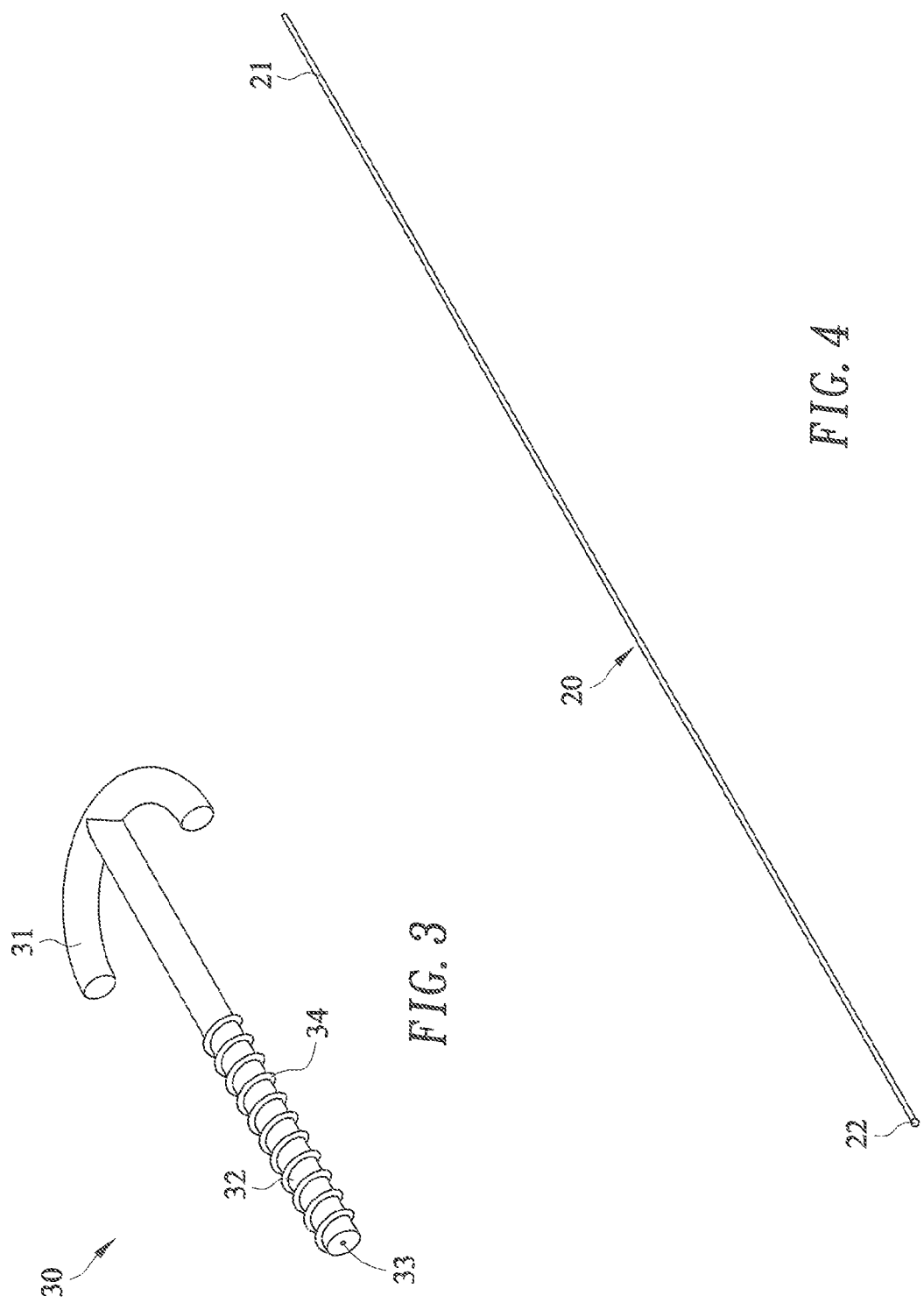

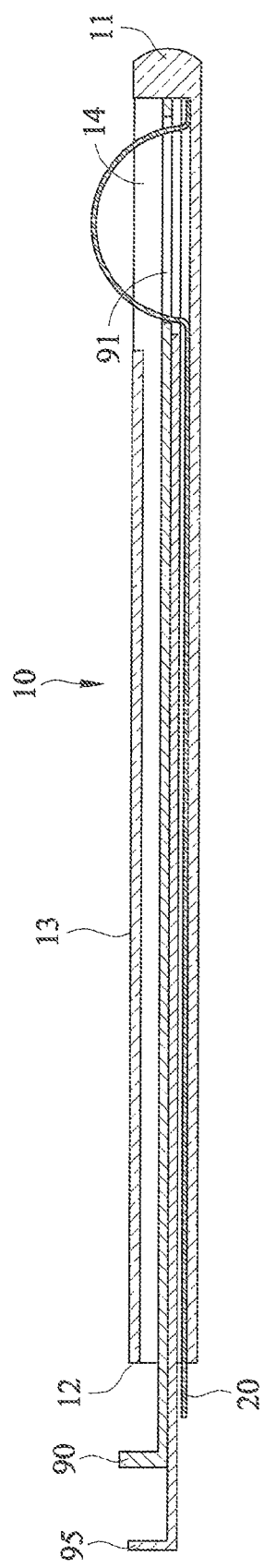

DEVICE AND METHOD FOR CUTTING INTO A CANCELLOUS BONE

FIELD OF THE INVENTION

The present invention is related to a tool for cutting into a cancellous bone, whereby soft tissues therein are broken into pieces to facilitate the migration/penetration of an orthopaedic paste. Without being broken, these soft tissues may hinder the migration/penetration of the orthopaedic paste in the bone being treated. The orthopaedic paste will set to act as a medical implant.

BACKGROUND OF THE INVENTION

It is well accepted that bioresorbable orthopedic implants are always the better choice than permanent foreign-body implants, as long as their bioresorption rates, biomechanical properties and variations in biomechanical properties with respect to the resorption processes are appropriately controlled. Among all bioresorbable orthopedic implants, calcium-based implants (calcium phosphate, calcium sulfate, etc.), are among the top choices so far. Some popular conventional methods of forming a hardened (set) bone cement in bone cavity involve creating a bone cavity in advance.

Prior-art cavity creation devices having an inflatable and expandable fluid-filled balloon structure often have insufficient "lift"—ability to push back compression—fractured bone (e.g., to restore vertebral body height) under certain circumstances due to the "softness" and the relatively large surface of the balloon. These devices do not have the function of cutting into the cancellous portion of a bone.

Prior-art cavity creation devices having an inflatable and expandable balloon-type structure rely on a high pressure fluid to expand a cavity in bone, which increases various high pressure-related risks in clinical procedures. These devices do not have the function of cutting into the cancellous portion of a bone.

Prior-art cavity creation devices having a foldable and extendable (expandable) rigid structure have risks of generating stress-concentrated spots and fresh cracks in the readily fractured bone. These devices do not have the function of cutting into the cancellous portion of a bone.

Most prior-art rigid-structure cavity creation devices have a hollow structure under expanded/unfolded condition. Once bone chips/fragments are trapped in such devices during unfolding (expanding) and/or folding (collapsing) procedures, such devices have risks of being unable to be retrieved from the treated site, especially through a minimally invasive percutaneous path. Likewise, in case any pieces/components of the rigid-structure devices break off the structure during procedure, these broken-off pieces/components would be very hard to be retrieved, especially through a minimally invasive percutaneous path. These devices do not have the function of cutting into the cancellous portion of a bone.

The inventors of the present application in WO 2006/138398 A2 disclose a non-inflated tool for expanding a bone cavity in which an orthopaedic paste is to be implanted comprising a flexible linear filler and a rod with one end thereof connected to one end of the flexible linear filler, so that the flexible linear filler can be pushed by the rod through a tube into a hole of a bone to expand a bone cavity in the bone. The filler may be a wire, band, or chain. Preferably, the chain comprises a series of beads linked one after another or by a string. Despite the ability of this non-inflated tool to effectively create/expand bone cavity, once the linear filler breaks, it would be very hard to retrieve the broken-loose bodies, especially through a minimally invasive percutaneous path. Another risk for the prior-art non-inflated tool is entanglement of the linear filler, which might happen during feeding (expansion) and/or retrieving procedure. When entanglement happens, it would be very hard for the linear filler to be retrieved, especially through a minimally invasive percutaneous path. These devices do not have the function of cutting into the cancellous portion of a bone.

The inventors of the present application in WO 2009/035549 A disclose a method of using beads to create a cavity in a bone comprising the following steps: a) introducing said beads into a bone by applying a pressure on said beads, wherein said beads are metallic beads able to be attracted by a magnet; and b) withdrawing said beads from said bone by magnetic force. In this prior art a tool is disclosed to facilitate the introduction said beads into a bone. These devices do not have the function of cutting into the cancellous portion of a bone.

For most prior-art rigid-structure cavity creation devices, an easy, accurate, reliable and safe bone-cavity creation procedure for a fractured bone or a bone suffering osteoporosis is always a great challenge. There is a need in developing an easy, accurate, reliable and safe technique for cutting into the cancellous portion of a bone, whereby soft tissues therein may be broken into pieces to facilitate the migration/penetration of an orthopaedic paste. Without being broken, these soft tissues may hinder the migration/penetration of the orthopaedic paste in the bone being treated. The orthopaedic paste will set to act as a medical implant.

SUMMARY OF THE INVENTION

A primary object of the present invention is to provide a method and device for cutting into the cancellous portion of a bone, (for example, a fractured vertebral body and a bone suffering osteoporosis), in which a sufficient amount of an orthopaedic paste is to be implanted in the bone by injection. Preferred embodiments of the present invention include (but not limited to) the features recited in the pending claims.

BRIEF DESCRIPTION OF THE DRAWINGS

FIG. 3 is a schematic perspective view showing a driver of the wire cutter shown in FIG. 1.

FIG. 4 is a schematic perspective view showing an elastic wire of the wire cutter shown in FIG. 1.

FIG. 18 is a cross-sectional view showing the wire cutter shown in FIG. 17.

DETAILED DESCRIPTION OF THE INVENTION

The present invention discloses a new technique for creating a cavity in a bone, and in particular in cancellous bone, so that the quantity of an orthopaedic paste to be implanted in the bone by injection can be increased remarkably in comparison with the bone without creating a cavity.

A wire cutter 100 for creating a cavity in a bone constructed according to a first preferred embodiment of the present invention is shown in FIG. 1 to FIG. 4. The wire cutter 100 has a restrainer 10, an elastic wire 20, and a driver 30.

Figure 1:
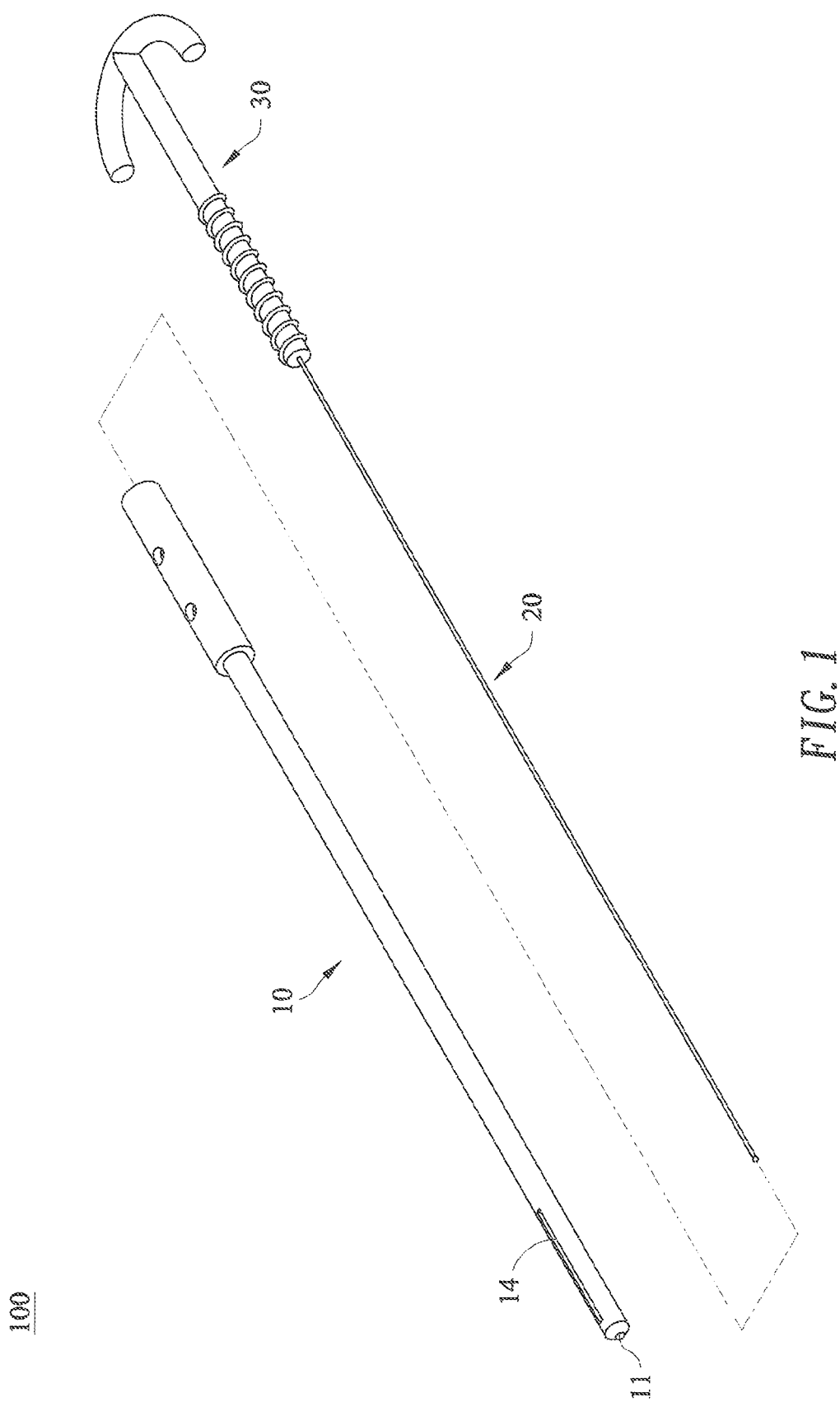
FIG. 1 is a schematic perspective view showing a wire cutter embodied according to a first preferred embodiment of the present invention.
Figure 2:
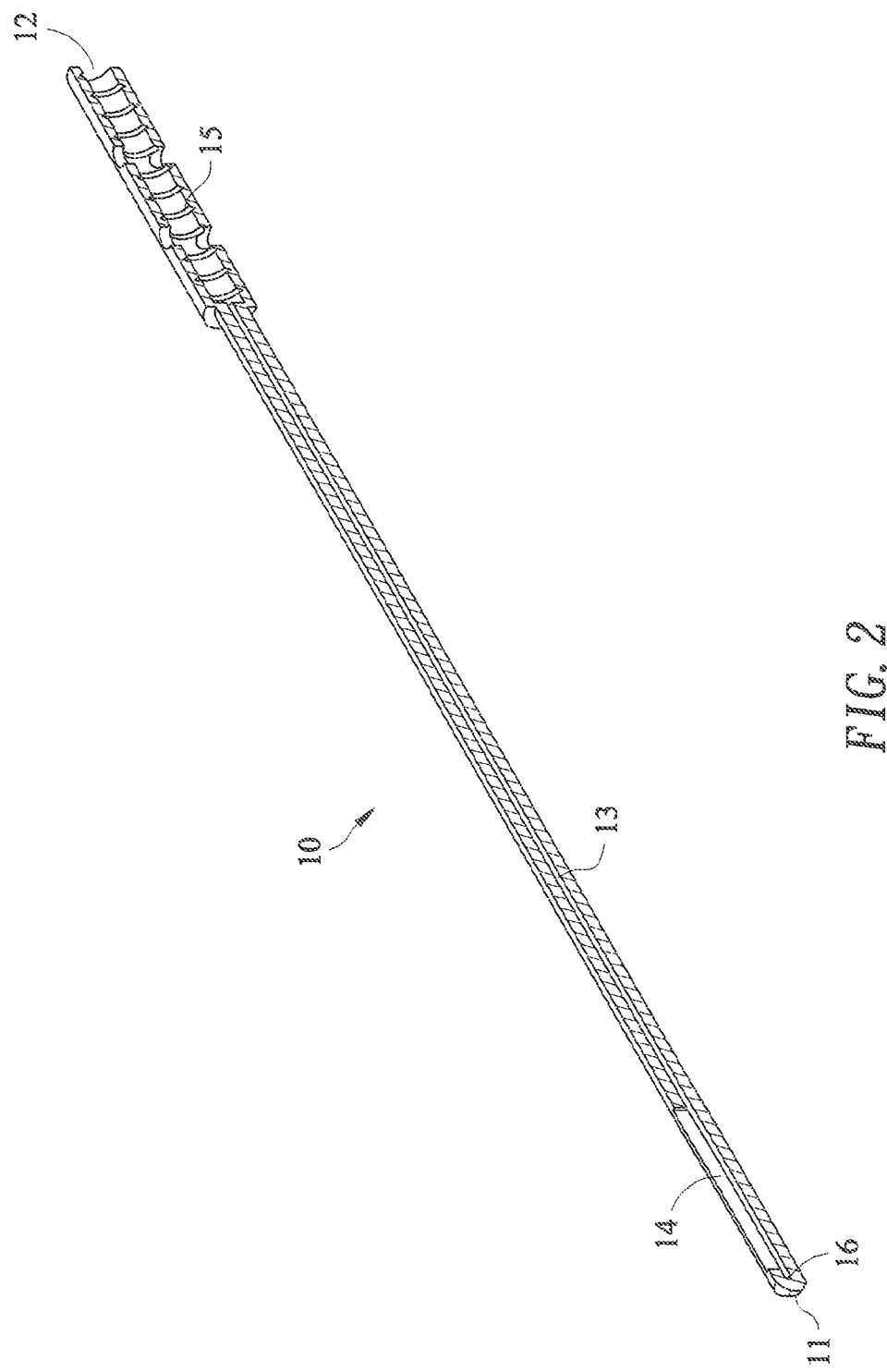
FIG. 2 is a cross-sectional view showing a restrainer of the wire cutter shown in FIG. 1.
Figure 5:
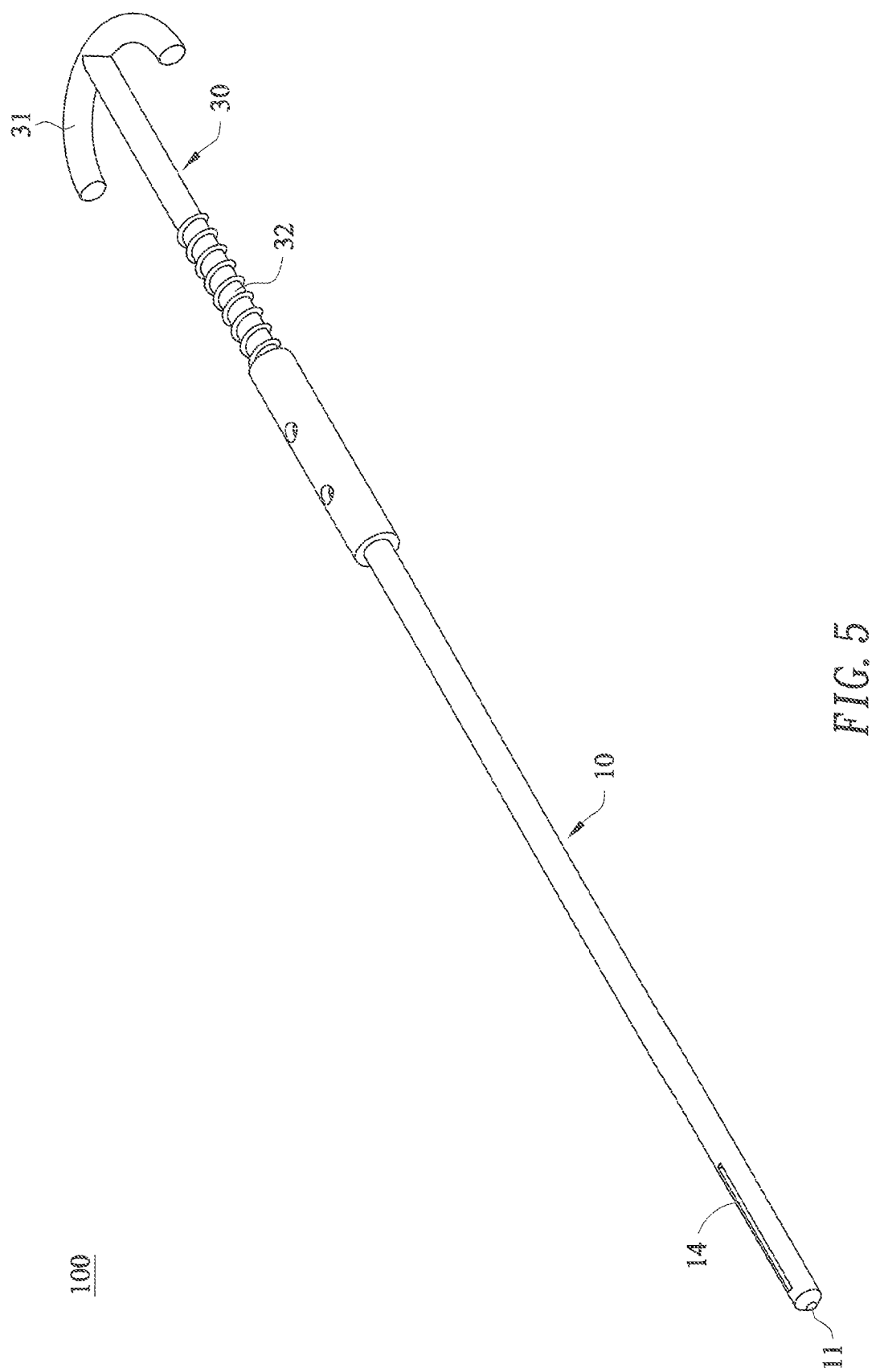
FIG. 5 is a schematic perspective view showing an initially engaged stage of the wire cutter shown in FIG. 1.

As shown in FIG. 2, the restrainer 10 has a closed end 11, an opening 12, a tunnel 13 inside the restrainer and from the opening 12 till the closed end 11, and a slot 14 parallel to the tunnel 13 which forms a passage from the tunnel 13 to an outside of the restrainer 10. The restrainer 10 is further provided with threads 15 on an inner wall of the tunnel 13 and near the opening 12, and with a round recess 16 at the closed end 11.

As shown in FIG. 3 and FIG. 4, the driver 30 has a handle 31, and a threaded stud 32 having a central mounting hole 33 axially along the threaded stud 32, and threads 34 formed on an outside wall of the threaded stud 32. The elastic wire 20 has a holding segment 21 which is rotatably received in the central mounting hole 33 of the threaded stud 32, and an enlarged spherical end 22 corresponding to the round recess 16 at the closed end 11 of the restrainer 10 (shown in FIG. 2), so that the enlarged spherical end 22 of the elastic wire 10 is able to be slightly clamped in the round recess 16 at the closed end 11 of the restrainer 10.

The aforesaid wire cutter 100 can be used to create a cavity in a bone having a pre-drilled hole (not shown in the drawings). As shown in FIG. 5 to FIG. 8, the elastic wire 20 is inserted into the tunnel 13 by holding the handle 31 of the driver 30. The driver 30 is rotated clockwisely when the threaded stud 32 contacts the opening 12 of the restrainer 10, so that the driver 30 is threadedly connected to the restrainer 10, and thus the wire cutter 100 is assembled. Then, the assembled wire cutter 100 is inserted into the bone via said pre-drilled hole, so that the slot 14 is inside the bone.

Alternatively, the restrainer 10 is first inserted into the bone via said pre-drilled hole, so that the slot 14 is inside the bone. Then, the elastic wire 20 is inserted into the tunnel 13 and the driver 30 is rotated clockwisely to assemble the wire cutter 100. As the clockwise rotation of the driver 30 continues, the holding segment 21 of the elastic wire 20 is advanced into the tunnel 13 of the restrainer 10, while the enlarged spherical end 22 of the elastic wire 20 is being stopped by the closed end 11 of the restrainer 10.

Figure 6:
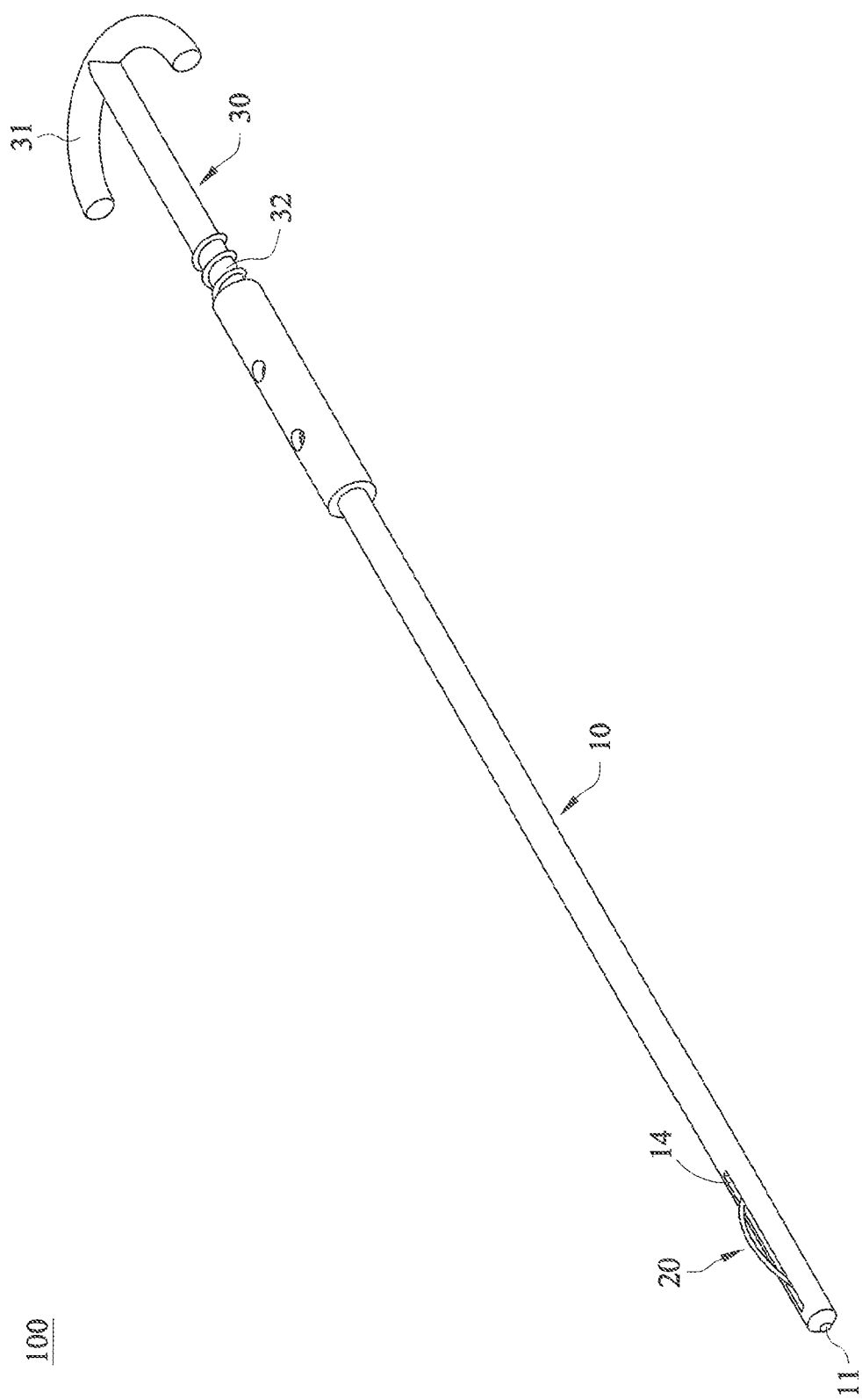
FIG. 6 is a schematic perspective view showing an intermediately engaged stage of the wire cutter shown in FIG. 1.

The clockwise rotation of the driver 30 is continued further until a portion of the elastic wire 20 protrudes from the slot 14 to the outside of the restrainer 10, as shown in FIG. 6. The protruded portion of the elastic wire 10 is inside the bone now. Cancellous portion of the bone will be cut by the protruded portion of the elastic wire 20, when the restrainer 10 and the driver 30 are rotated together.

Figure 7:
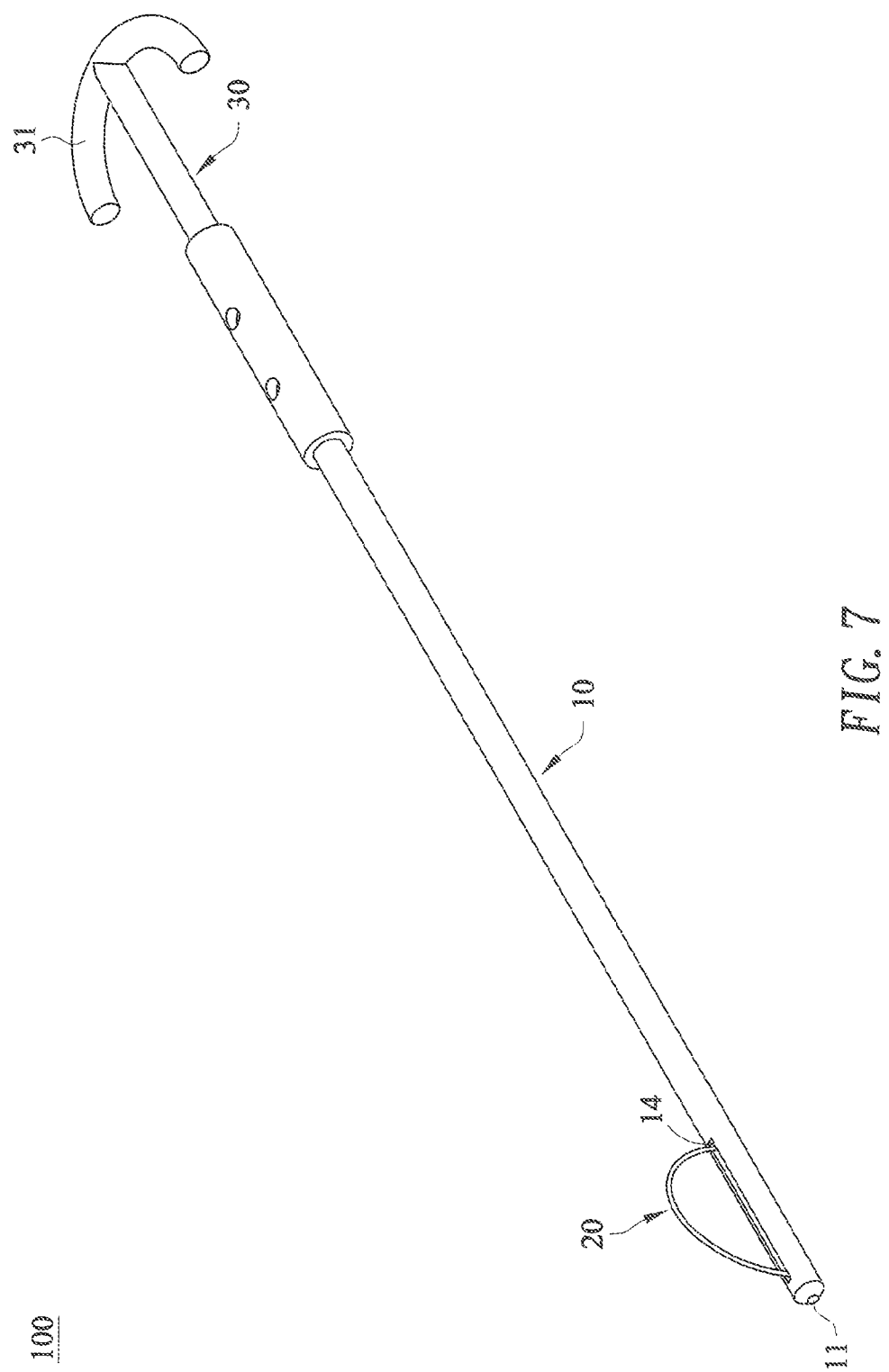
FIG. 7 is a schematic perspective view showing a fully engaged stage of the wire cutter shown in FIG. 1.
Figure 8:
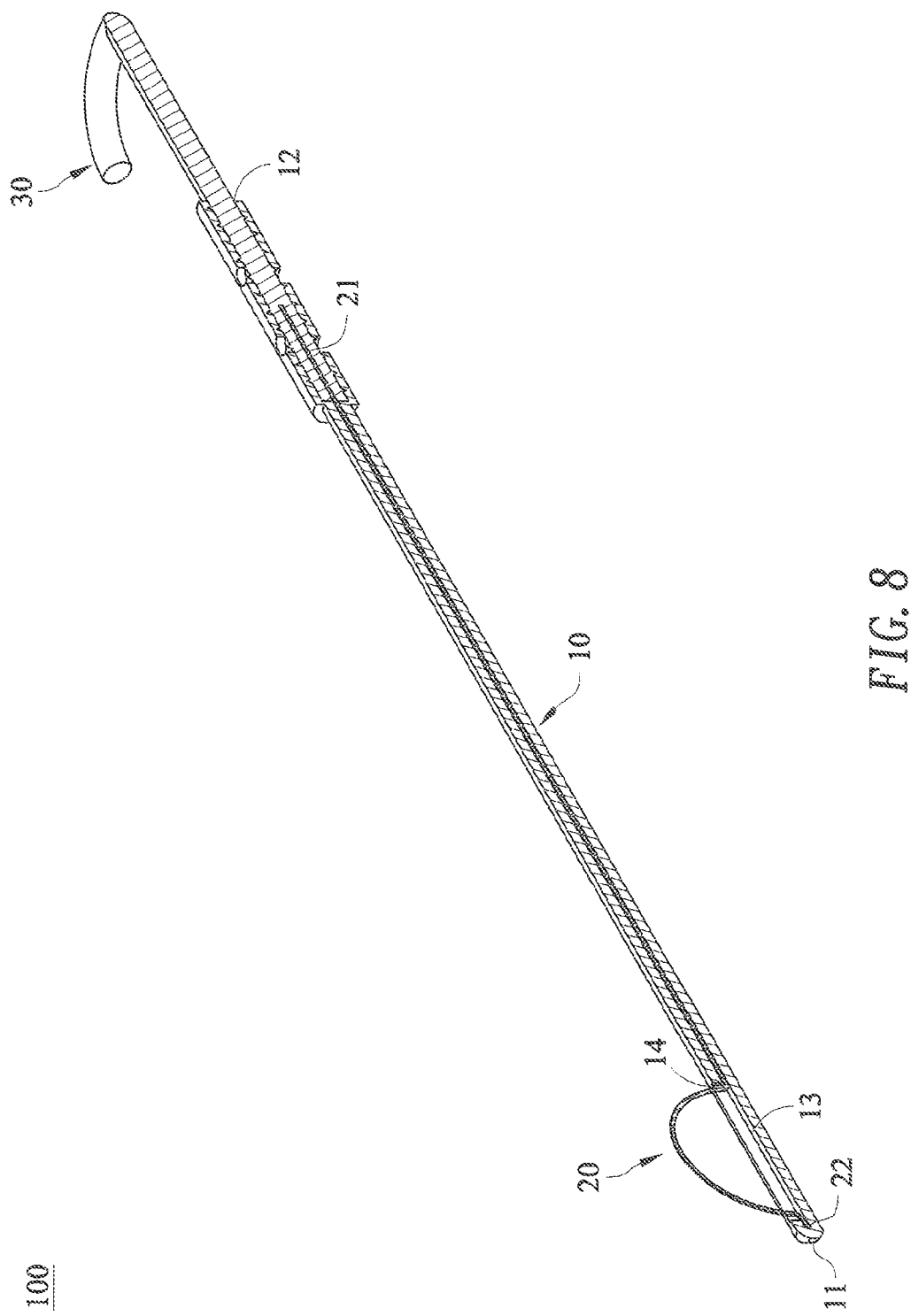
FIG. 8 is a schematic cross-sectional view showing the wire cutter shown in FIG. 7.

As shown in FIGS. 7 and 8, the holding segment 21 of the elastic wire 20 is advanced closer to the closed end 11 of the restrainer 10, so that a greater portion of the elastic wire 20 protrudes from the slot 14 to the outside of the restrainer 10. Greater cancellous portion of the bone will be cut by the greater protruded portion of the elastic wire 10 by rotating the restrainer 10 and the driver 30 together. The protruded (rotation-cut) portion gradually increases while the wire continues to gradually advance until a desired volume of cavity is created. After that, the protruded portion of the elastic wire 20 can be retrieved from the cavity by rotating the driver 30 counterclockwisely.

The elastic wire 20 is preferably a biocompatible, high strength metallic wire (e.g., a 316L stainless steel wire or a titanium/titanium alloy wire) having a diameter of about 0.20 mm to 3.0 mm; preferably 0.3 mm to 2.0 mm; and more preferably 0.4 mm to 1.5 mm. The elastic wire 20 has a sufficient strength so that it will not be broken into two pieces, and it will bend and a portion thereof will protrude from the slot 14 when the driver 30 is rotated clockwisely as described above. A certain degree of elasticity of the elastic wire 20 is preferred, so that the bent elastic wire can resume a straight line as the driver 30 is rotated counterclockwisely, making retrieval of the wire cutter 100 from the bone easier. The elastic wire 20 is not necessarily a fully elastic wire. A certain degree of plastic deformation may be allowed, as long as it can be retrieved through the restrainer 10. The portion of the cutting wire protruding from the slot has a shape of an arch similar to a rainbow. The cutting wire protruding from the slot may have an inverted U-shape shape, when at least a portion of the cutting wire protruding from the slot is thicker than the rest portion of the cutting wire protruding from the slot.

The rotation-cutting method of the present invention can create a cavity by breaking the soft tissue network of a cancellous portion of a bone, which readily forms overtime for a chronic case. Without breaking loose the soft tissue network, cement is often very hard to be injected into the bone.

The diameter of the elastic wire 20 should be as close to a diameter of the tunnel 13 of the restrainer 20 as possible, so that the advancement of the elastic wire 20 in the tunnel 13 may be easier (without being bent in the tunnel 13 of the restrainer 10 during the advancement).

The slot 14 should have a width as close to the diameter of the elastic wire 20 as possible, so that the cutting ability is maximized by the slot inner wall support (without being bent inside the slot during cutting (rotation)). The slot 14 should also has a depth as large as possible to increase the support of the slot wall during cutting (rotation).

A reasonable prototype device would be:

316L stainless steel wire with diameter about 1 mm;
316L stainless steel tube with inner diameter slightly larger than 1 mm and outer diameter about 3 mm; and
the slot depth about 1 mm.

Figure 9:
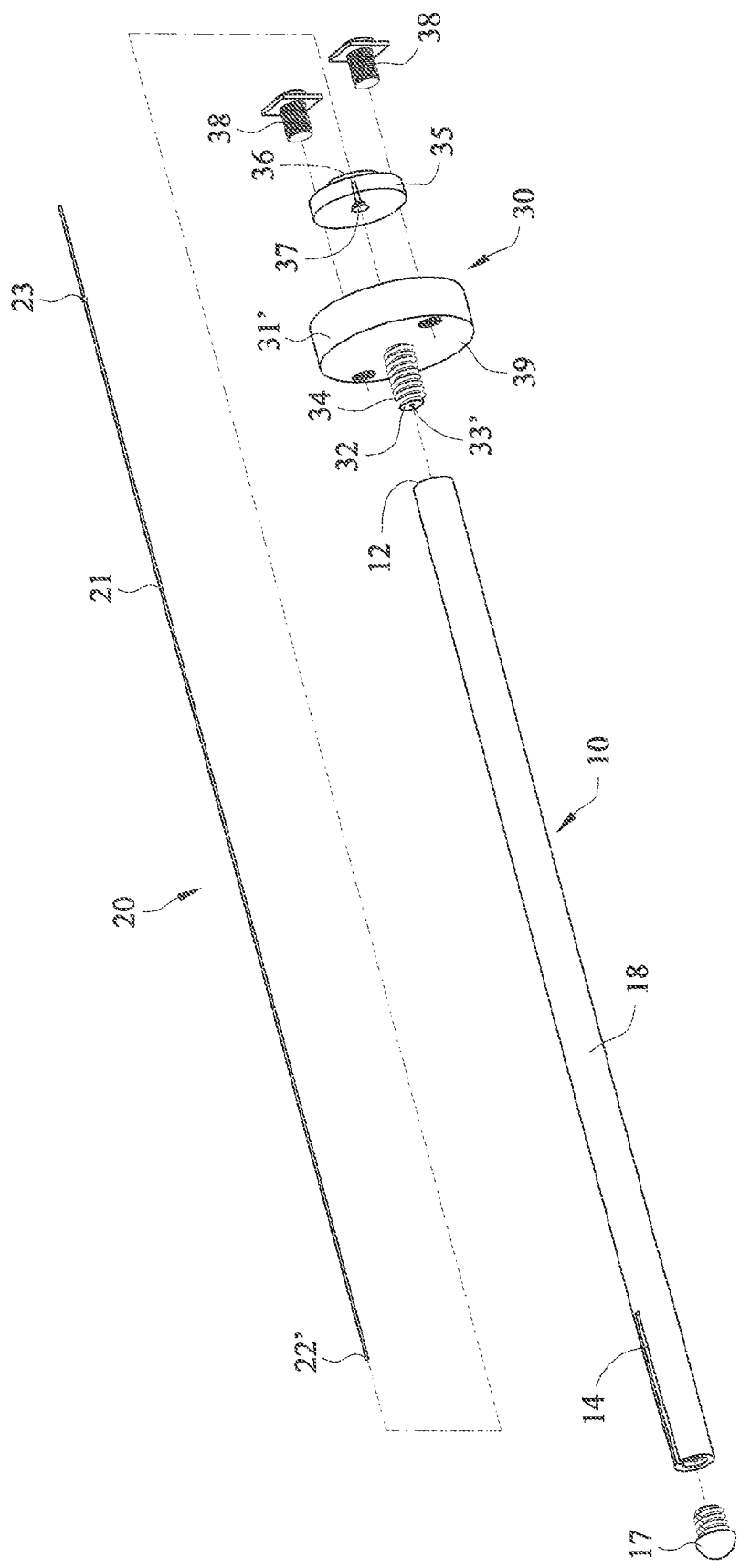
FIG. 9 is a schematic perspective view showing a wire cutter embodied according to a second preferred embodiment of the present invention.
Figure 10:
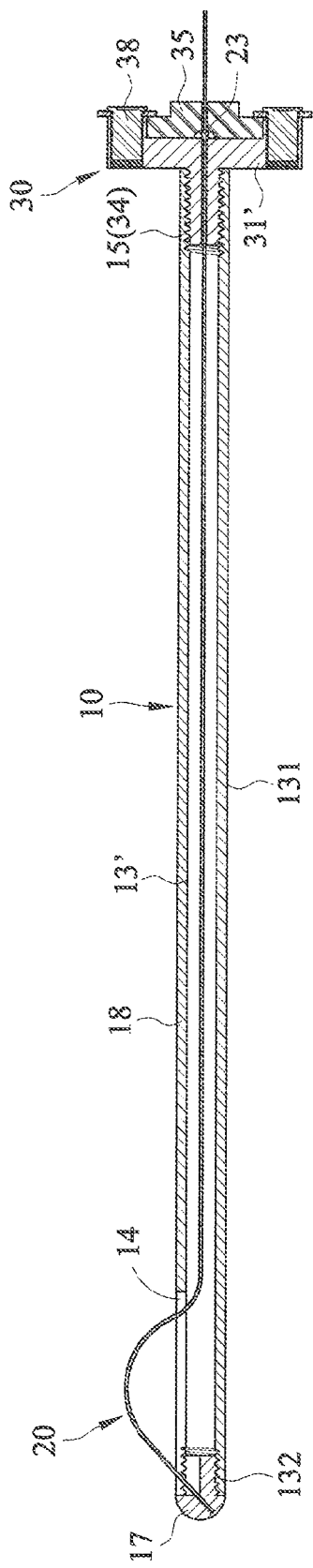
FIG. 10 is a cross-sectional view showing the wire cutter shown in FIG. 9.
Figure 11:
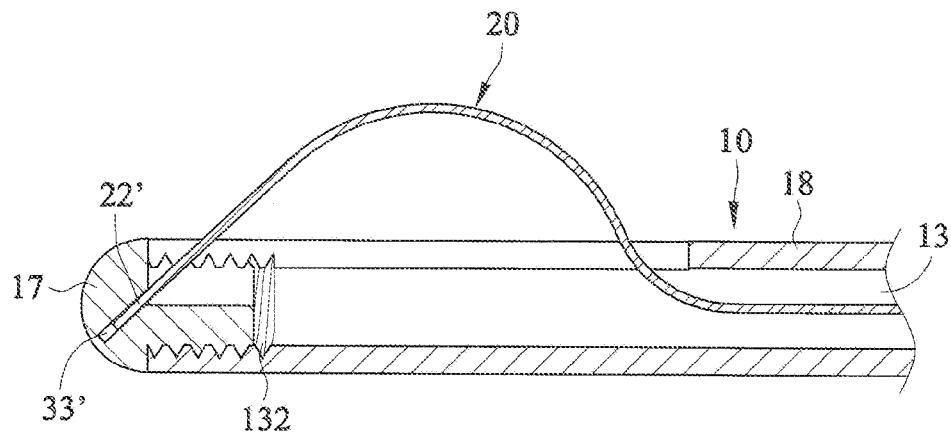
FIG. 11 is an enlarged partial cross-sectional view showing the closed end of the wire cutter shown in FIG. 10.
Figure 12:
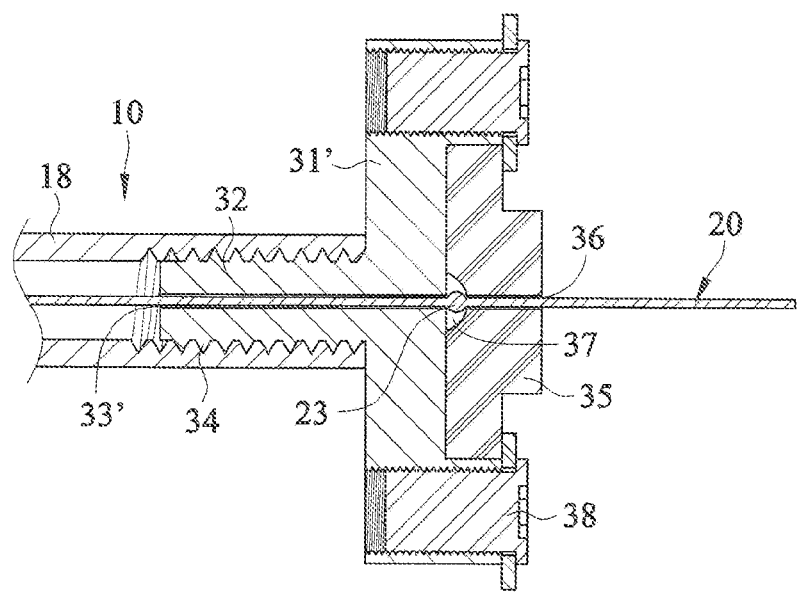
FIG. 12 is an enlarged partial cross-sectional view showing the proximal end of the wire cutter shown in FIG. 10.

A wire cutter 200 constructed in accordance with a second preferred embodiment of the present invention is shown in FIG. 9 and FIG. 10, which is similar to the wire cutter 100 constructed according to the first preferred embodiment of the present invention, wherein like elements in the two embodiments are represented by like numerals.

As shown in FIG. 9 to FIG. 12, the wire cutter 200 has a restrainer 10, an elastic wire 20, and a driver 30. The driver 30 has a disc 31', a cover 35, and a pair of bolts 38 for fastening the cover 35 to the disc 31'. The disc 31' has a threaded stud 32 located concentrically on one side of the disc 31'. A central mounting hole 33' which is a through hole is formed axially along the threaded stud 32 and the disc 31'. The threaded stud 32 is provided with threads 34 on an outside wall thereof. The cover 35 has a central through hole 36 corresponding to the central mounting hole 33' of the disc 31', wherein an enlarged dome-shaped opening 37 is provided at one end of the central through hole 36. The elastic wire 20 has a distal end 22', a holding segment 21 close to another end, and a spherical flange 23 on the holding segment 21, wherein the elastic wire 20 has a diameter slighter smaller than that of the central mounting hole 33' of the disc 31'/the central through hole 36 of the cover 35, and the spherical flange 23 has a diameter larger than that of the central mounting hole 33' of the disc 31'/the central through hole 36 of the cover 35. At the same time, the spherical flange 23 is smaller than the dome-shaped opening 37. Accordingly, the distal end 22' of the elastic wire 20 is able to be inserted into the central mounting hole 33' of the disc 31', until the spherical flange 23 is stopped by the disc 31'. The cover 35 is then put on the elastic wire 20 with the holding segment 21 being received in the central through hole 36 of the cover 35 and the spherical flange 23 being accommodated in the dome-shaped opening 37. The pair of bolts 38 are then threaded into two threading bores 39, so that the cover 35 is fastened to the disc 31', and the elastic wire 20 is rotatably connected to the driver 30.

The restrainer 10 is formed by two parts, a closed end part 17 and a major part 18, wherein the closed end part 17 is threadedly connected to the major part 18. The tunnel 13' of the restrainer 10 has a major straight segment 131 in the major part 18 followed by a bent segment 132 in the closed end part 17 of the restrainer 10, wherein an angle between an imaginary extension of the straight segment 131 and the bent segment 132 of the tunnel 13' is about 45°. The restrainer 10 is further provided with an opening 12 opposite to the closed end part 17, and threads 15 on an inner wall of the tunnel 13' and near the opening 12.

The elastic wire 20 with its holding segment 21 rotatably received in the driver 30 is inserted into the tunnel 13' of the restrainer 10 by holding the driver 30. A distal end 22' of the elastic wire 20 will enter the bent segment 132 of the tunnel 13' as the threaded stud 32 contacts the opening 12 of the restrainer 10 and is threaded into the tunnel 13'. As the driver 30 is driven closer to the opening 12 of the restrainer 10, a greater portion of the elastic wire 20 will protrude from the slot 14 to the outside of the restrainer 10. The bent segment 132 of the tunnel 13 is helpful for forming the protruded portion of the elastic wire 20, when the threaded stud 32 is threaded into the tunnel 13'; and is also helpful for rotating the protruded portion of the elastic wire 20, when the restrainer 10 is rotated.

Figure 13:
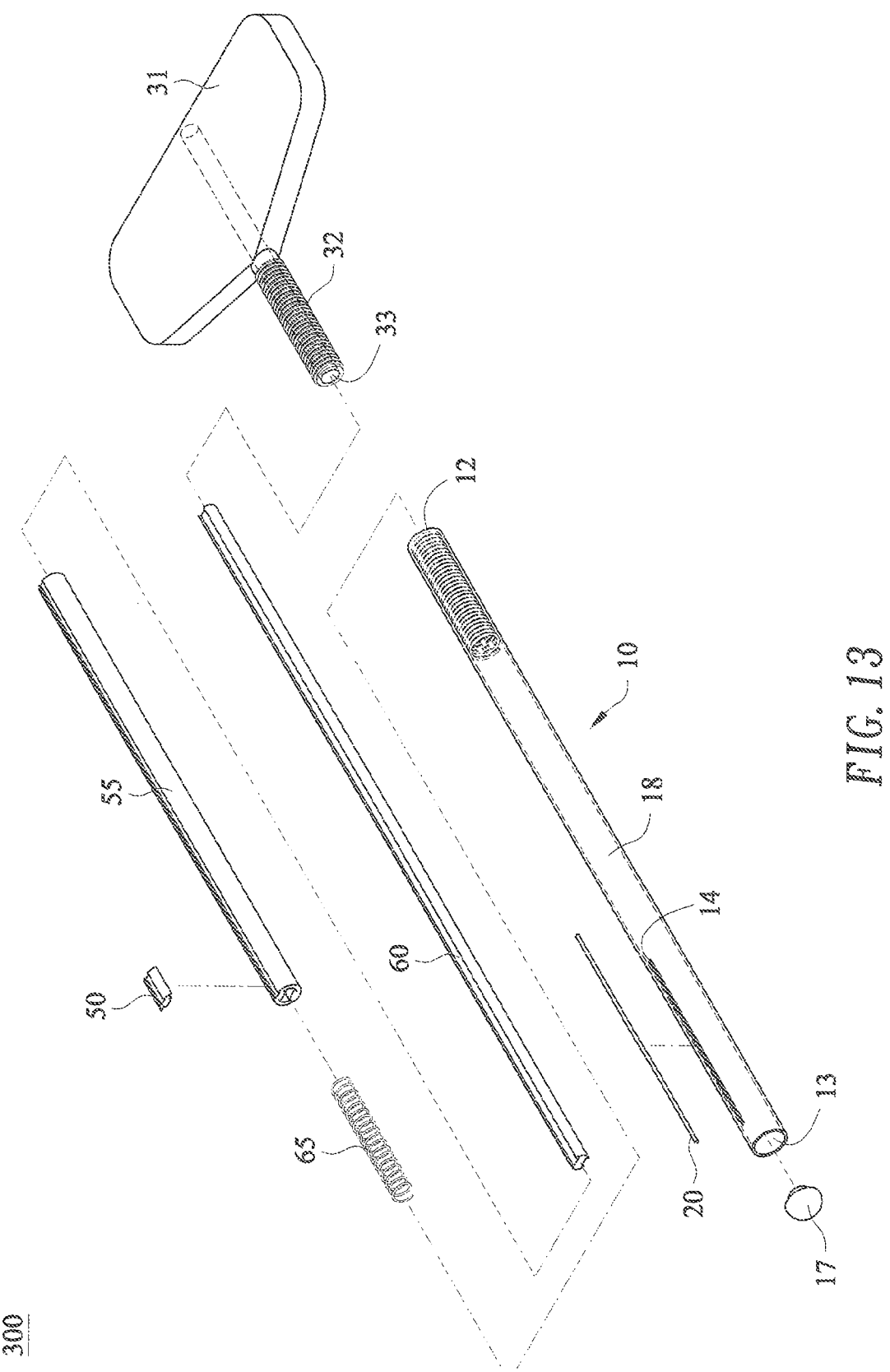
FIG. 13 is a schematic perspective view showing a wire cutter embodied according to a third preferred embodiment of the present invention.
Figure 14A:
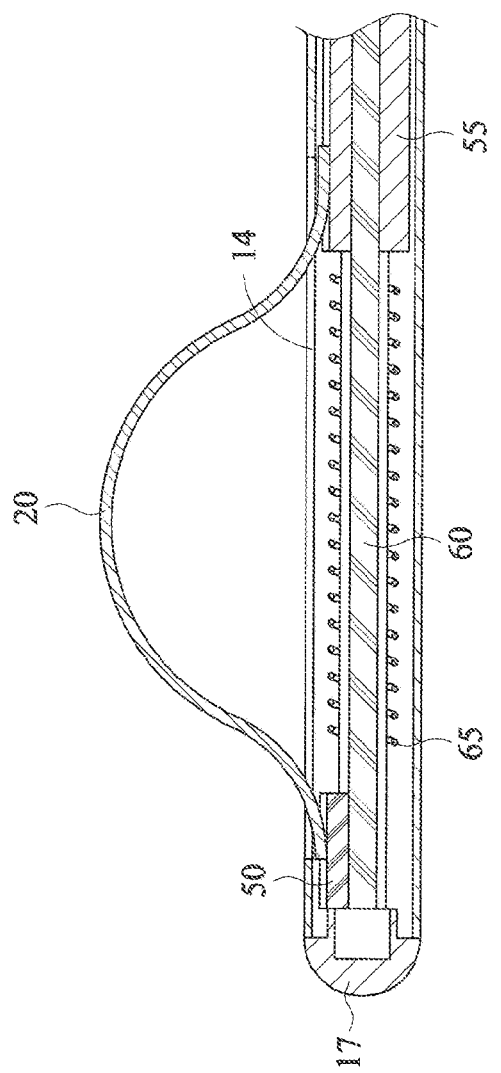
FIG. 14A is an enlarged cross-sectional view showing the closed end of the wire cutter shown in FIG. 13.
Figure 14B:
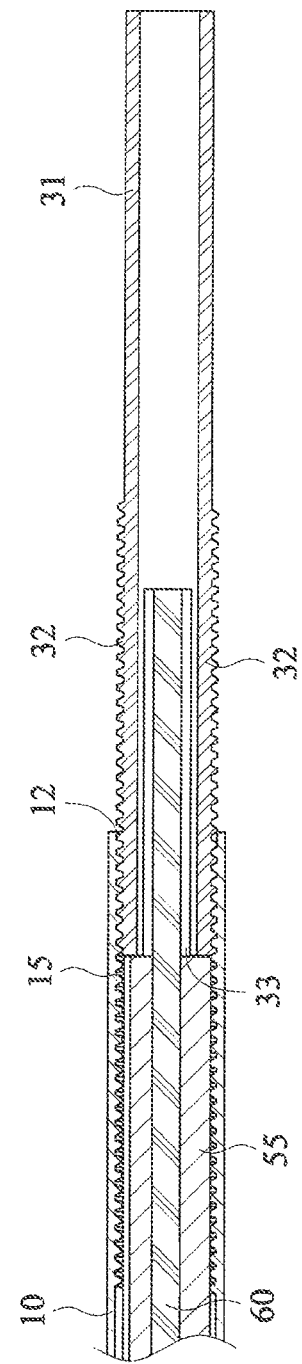
FIG. 14B is an enlarged cross-sectional view showing the proximal end of the wire cutter shown in FIG. 13.

A wire cutter 300 constructed in accordance with a third preferred embodiment of the present invention is shown in FIGS. 13, 14A and 14B, wherein a much shorter cutting wire is adopted in comparison with the cutting wires used in the aforesaid first and second embodiments. The wire cutter 300 has a restrainer 10, an elastic wire 20, and an advancing mechanism.

The restrainer 10 is formed by two parts, a closed end part 17 and a major part 18, wherein the closed end part 17 is threadedly connected to or tightly plugged into the major part 18. The restrainer 10 has an opening 12, and a tunnel 13 inside the restrainer and from the opening 12 till the closed end part 17, and a slot 14 parallel to the tunnel 13 which forms a passage from the tunnel 13 to an outside of the restrainer 10.

The advancing mechanism shown in FIGS. 13, 14A and 14B includes a first wire holder 50 holding the distal end of the cutting wire 20 by soldering; a second wire holder 55 holding the holding segment of the cutting wire 20 by soldering; a central rod 60; a compression spring 65; threads 15 formed in the opening of the tunnel 13 of the restrainer 10; and a threaded stud 32 having an axial mounting hole 33 at one end thereof, and a handle 31 at another end thereof, wherein the central rod 60 is received in the tunnel 13 of the restrainer with one end thereof being stopped by the closed end part 17 of the restrainer and another end thereof protruding from the opening 12 of the restrainer 10, the first wire holder 55 is slidably received on the central rod 60 with one end of being stopped by the closed end part 17 of the restrainer, the compression spring 65 is slidably received on the central rod 60 with one end of being stopped by another end of the first wire holder 50, the second wire holder 55 is slidably received on the central rod 60 with one end thereof being stopped by another end of the compression spring 65, and the threaded stud 32 is threadedly received in the opening 12 of the restrainer with the protruding end of the central rod 60 being received in the mounting hole 33 of the threaded stud by rotating the handle 31 of the threaded stud in relative to the restrainer 10, wherein the second wire holder 55 will be pressed by the threaded stud 32 and moved toward the closed end part 17 of the restrainer as the rotation of the handle 31 of the threaded stud is continued, so that the compression spring 65 is compressed by the second wire holder 55 and the first wire holder 50, and thus the cutting wire 20 is pressed by the second wire holder 55 and protrudes from the slot 14 to the outside of the restrainer 10. In order to prevent the relative rotation between the central rod 60 and the first wire holder 50 and the second wire holder 55, the central rod 60 is provided with a pair of opposite grooves on its outer surface, and the first wire holder 50 and the second wire holder 55 are both provided with a pair of opposite ridges corresponding to the grooves on the inner walls of the through holes of the first wire holder 50 and the second wire holder 55. Further, the closed end part 17 is provided with a recess to grasp the distal end of the central rod 60 by friction/elasticity.

Figure 15:
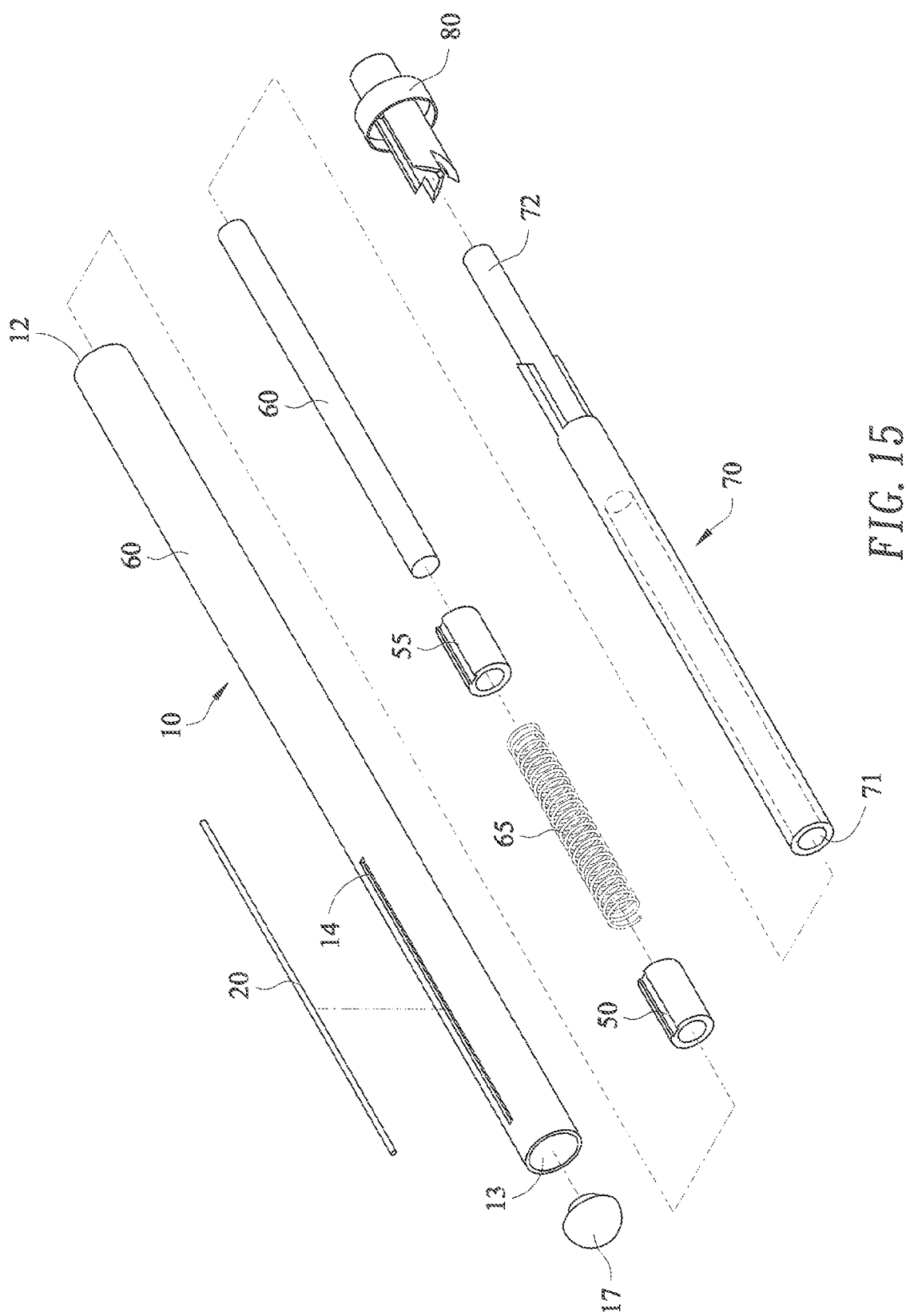
FIG. 15 is a schematic perspective view showing a wire cutter embodied according to a fourth preferred embodiment of the present invention, wherein the restrainer is not shown.
Figure 16:
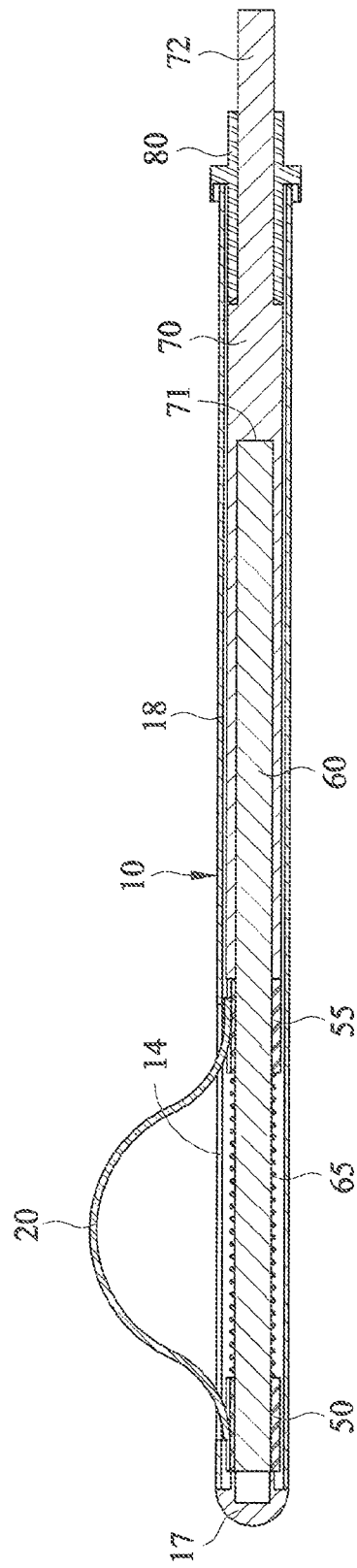
FIG. 16 is a cross-sectional view showing the wire cutter shown in FIG. 15.

A wire cutter 400 constructed in accordance with a fourth preferred embodiment of the present invention is shown in FIG. 15 and FIG. 16, wherein a different advancing mechanism similar to that used in the conventional automatic ball pens is adopted. The wire cutter 400 has a restrainer 10, an elastic wire 20, and an advancing mechanism.

The restrainer 10 is formed by two parts, a closed end part 17 and a major part 18, wherein the closed end part 17 is threadedly connected to or tightly plugged into the major part 18. The restrainer 10 has an opening 12, and a tunnel 13 inside the restrainer and from the opening 12 till the closed end part 17, and a slot 14 parallel to the tunnel 13 which forms a passage from the tunnel 13 to an outside of the restrainer 10.

The advancing mechanism shown in FIGS. 15 and 16 includes a first wire holder 50 holding the distal end of the cutting wire 20; a second wire holder 55 holding the holding segment of the cutting wire 20; a central rod 60; a compression spring 65; threads 15 formed in the opening of the tunnel 13 of the restrainer 10; and a clutch rod 70 having an axial mounting hole 71 at one end thereof, and a pushing end 72 at another end thereof; and a control tubular element 80, wherein the central rod 60 is received in the tunnel 13 of the restrainer with one end thereof being stopped by the closed end part 17 of the restrainer, the first wire holder 50 is slidably received on the central rod 60 with one end of being stopped by the closed end part 17 of the restrainer, the compression spring 65 is slidably received on the central rod 60 with one end of being stopped by another end of the first wire holder 50, the second wire holder 55 is slidably received on the central rod 60 with one end thereof being stopped by another end of the compression spring 65, the clutch rod 70 is inserted into the tunnel 13 of the restrainer via the opening 12 of the restrainer with the mounting hole 71 of the clutch rod accommodating another end of the central rod 60 and the pushing end 72 protruding from the opening 12 of the restrainer, and the control tubular element 80 is fixedly connected to the opening 12 of the restrainer with the pushing end 72 of the clutch rod protruding from the control tubular element 80, wherein a clutch mechanism is provided on an outer surface of the clutch rod and on the control tubular element, so that the clutch rod 70 is able to be stopped by the control tubular element 80 at various positions in relative to the closed end part 17 of the restrainer when the clutch rod 70 is pushed back by the compression spring 65 which has be deformed by pushing the pushing end 72 of the clutch rod toward the closed end part 17 of the restrainer, wherein the various positions comprise an advanced position where the compression spring 65 is compressed at a relatively greater extent, so that the cutting wire 20 is pressed by the second wire holder 55 and protrudes from the slot 14 to the outside of the restrainer; and a release position where the compression spring 65 is compressed at a relatively less extent, so that the cutting wire 20 is released from the press by the second wire holder 65 and dives from the slot 14 into the tunnel 13 of the restrainer.

Figure 17:
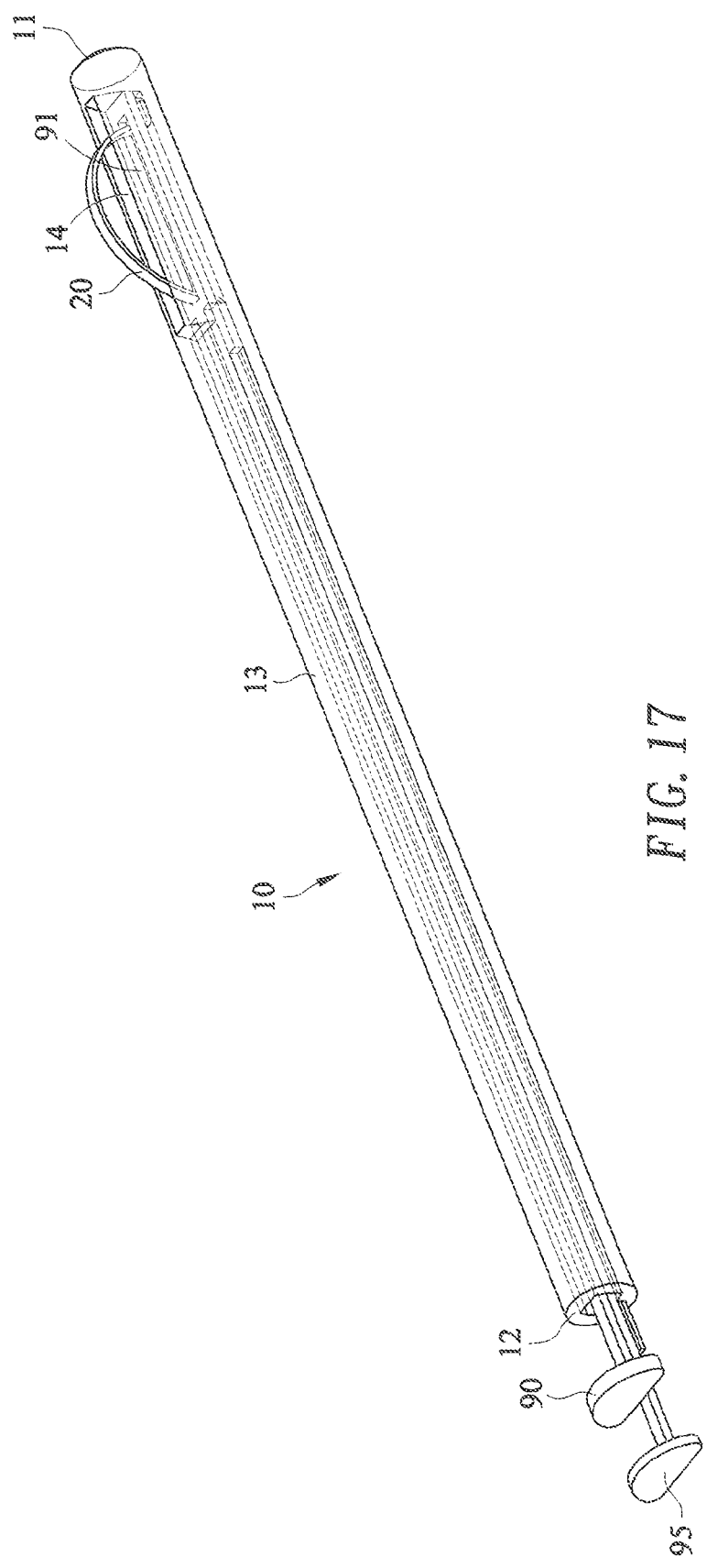
FIG. 17 is a schematic perspective view showing a wire cutter embodied according to a fifth preferred embodiment of the present invention. For the illustration purpose, the restrainer is assumed being transparent.

As shown in FIGS. 17-18, a wire cutter constructed according to a fifth preferred embodiment of the present invention is further provided with a slot adjustment mechanism, including a slot front adjuster 90 and a slot rear adjuster 95.

The slot front adjuster 90 is a long narrow thin plate suitable to be inserted into the tunnel 13 of the restrainer 10 from the opening 12 to the closed end 11 thereof, wherein a distal end of the slot front adjuster 90 is provided with an adjusting slot 91 corresponding to the slot 14 of the restrainer 10. The slot front adjuster 90 can be used to adjust the span of an arch of the elastic wire 20 protruding from the slot 14 of the restrainer 10, when the slot front adjuster 90 is inserted into the tunnel 13 of the restrainer 10 before the elastic wire 20. The elastic wire 20 after being inserted into the tunnel 13 of the restrainer 10, as described before, will form a protruding arch from the adjusting slot 91 of the slot front adjuster 90 and the slot 14 of the restrainer 10 as shown in FIG. 17 and FIG. 18. It is apparent that the span of the protruding arch will become narrower, if a proximal end of the slot front adjuster 90 is pulled to withdraw the adjusting slot 91 of the slot front adjuster 90 from the closed end 11 of the restrainer 10 while holding the elastic wire 20 still. That is a front end of the protruding arch of the elastic wire 20 from the slot 14 of the restrainer 10 is retreated by using the slot front adjuster 90.

On the contrary, the slot rear adjuster 95 can be used to narrow the span of the protruding arch of the elastic wire 20 from the slot 14 of the restrainer 10 by pushing the rear end of the protruding arch of the elastic wire 20 forward. The slot rear adjuster 95 is a long narrow thin plate suitable to be inserted into the tunnel 13 of the restrainer 10 from the opening 12 to the closed end 11 thereof, wherein a distal end of the slot rear adjuster 95 is adapted to cover the slot 14 of the restrainer 10. The slot rear adjuster 95 can be used to adjust the span of an arch of the elastic wire 20 protruding from the slot 14 of the restrainer 10, when the slot rear adjuster 95 is inserted into the tunnel 13 of the restrainer 10 before or after the elastic wire 20. The elastic wire 20 after being inserted into the tunnel 13 of the restrainer 10, as described before, will form a protruding arch from the slot 14 of the restrainer 10 as shown in FIG. 17 and FIG. 18. It is apparent that the span of the protruding arch will become narrower, if a proximal end of the slot rear adjuster 95 is pushed to cover a part of the slot 14 of the restrainer 10 by the distal end of the slot rear adjuster 95 while holding the elastic wire 20 still. That is a rear end of the protruding arch of the elastic wire 20 from the slot 14 of the restrainer 10 is pushed forward by using the slot rear adjuster 95.

One can imagines that the position of the protruding arch of the elastic wire 20 from the slot 14 of the restrainer 10 can be adjusted by using the slot front adjuster 90 and the slot rear adjuster 95 together as shown in FIG. 17 and FIG. 18, wherein the front end of the protruding arch of the elastic wire 20 from the slot 14 of the restrainer 10 can be retreated by pulling the slot front adjuster 90, and the rear end of the protruding arch of the elastic wire 20 from the slot 14 of the restrainer 10 can be moved forward by pushing the slot front adjuster 90, while holding the elastic wire 20 still. Thereafter, height of the protruding arch of the elastic wire 20 from the slot 14 of the restrainer 10 can be increased, if the proximal end of the elastic wire 20 is pushed toward the closed end 11 of the restrainer while holding the slot front adjuster 90 and the slot rear adjuster 95 still.

The invention claimed is:

1. A wire cutter comprising a restrainer and a cutting wire, wherein the restrainer comprises an opening at a proximal end thereof, a closed end opposite to the proximal end, a tunnel inside the restrainer and from the opening till the closed end, and a slot parallel to the tunnel and forming a passage from the tunnel to an outside of the restrainer; and said cutting wire adapted to be received in the tunnel, wherein said cutting wire has a distal end and a holding segment away from the distal end, wherein the holding segment is able to be driven to move in the tunnel toward the closed end of the restrainer while the distal end of the cutting wire being stopped directly or indirectly by the closed end of the restrainer, so that a portion of the cutting wire will protrude from the slot to the outside of the restrainer, when the holding segment of the cutting wire is driven to move toward the closed end of the restrainer, wherein the wire cutter further comprises an advancing means for driving the holding segment of the cutting wire to move toward the closed end of the restrainer and to move away from the closed end after being driven to move toward the closed end of the restrainer, so that a greater portion of the cutting wire will protrude from the slot to the outside of the restrainer as the holding segment of the cutting wire is driven to move closer to the closed end of the restrainer,
wherein the distal end of the cutting wire is stopped directly by the closed end of the restrainer, the advancing means comprises threads formed on an inner wall of the tunnel of the restrainer and near the opening of the restrainer, and a threaded stud adapted to be in engagement with the threads, wherein the threaded stud is provided with an axial mounting hole adapted to accommodate the holding segment of the cutting wire, and
wherein the cutting wire is straight, and the tunnel of the restrainer has a major straight segment followed by a bent segment near the closed end of the restrainer, wherein an angle between an imaginary extension of the straight segment and the bent segment of the tunnel is ranging from 5° to 60°.

2. The wire cutter of claim 1, wherein the holding segment is clamped fixedly in the mounting hole of the threaded stud.

3. The wire cutter of claim 1, wherein the holding segment of the cutting wire is protruding from the opening of the restrainer, and the holding segment is rotatably received in the mounting hole of the threaded stud.

4. The wire cutter of claim 1, wherein the restrainer is formed at least by two parts, a closed end part and a major part, wherein the closed end part contains the closed end of the restrainer and is connected to the major part.

5. The wire cutter of claim 1, wherein the restrainer is formed at least by two parts, a closed end part and a major part, wherein the closed end part contains the closed end of the restrainer and the bent segment of the tunnel, and is threadedly connected to the major part.

6. The wire cutter of claim 1 wherein the cutting wire is a steel wire, a titanium or titanium alloy wire having a diameter or a width of 0.20 mm to 3.0 mm.

7. The wire cutter of claim 1 wherein the cutting wire has a cross section of a shape selected from circular, oval, square, rectangular, triangular, and hexagonal.

8. The wire cutter of claim 1 wherein the cutting wire has a cross section of a shape selected from circular, oval, square, rectangular, triangular, and hexagonal, wherein the portion of the cutting wire which will protrude from the slot has a cross-sectional area smaller than a cross-sectional area of the remaining portion of the cutting wire.

9. The wire cutter of claim 1, wherein the portion of the cutting wire protruding from the slot is arcuate.

10. The wire cutter of claim 1, wherein the portion of the cutting wire protruding from the slot has a shape of an arch or an inverted U-shape.

11. A method for creating a cavity in a bone comprising:
a) providing a wire cutter as set forth in claim 1;
b) setting up the wire cutter, so that the slot is inside a bone through a pre-drilled hole in the bone;
c) advancing the holding segment of the cutting wire into the tunnel and toward the closed end of the restrainer until a portion of the cutting wire protrudes from the slot to the outside of the restrainer and inside the bone; and
d) rotating the cutting wire, so that cancellous portion of the bone is cut by the protruding portion of the cutting wire.

12. The method claim 11, wherein step b) comprises:
b1) inserting the cutting wire into the tunnel with the distal end of the cutting wire being stopped by the closed end of the restrainer; and
b2) inserting the restrainer together with the cutting wire into the pre-drilled hole in the bone.

13. The method claim 11, wherein step b) comprises:
b3) inserting the restrainer into the pre-drilled hole in the bone; and
b4) inserting the cutting wire into the tunnel with the distal end of the cutting wire being stopped by the closed end of the restrainer.

14. The method of claim 11 further comprising repeating step c) and d), except that the holding segment of the cutting wire is advanced closer to the closed end of the restrainer, so that a greater portion of the cutting wire protrudes from the slot to the outside of the restrainer, and greater cancellous portion of the bone is cut by the greater protruded portion of the cutting wire.

15. The wire cutter of claim 1 further comprising a slot adjustment mechanism comprising a slot front adjuster, a slot rear adjuster, or a combination thereof, wherein the slot front adjuster is a long narrow thin plate suitable to be inserted into the tunnel of the restrainer from the opening to the closed end thereof, wherein a distal end of the slot front adjuster is provided with an adjusting slot corresponding to the slot of the restrainer;
the slot rear adjuster is a long narrow thin plate suitable to be inserted into the tunnel of the restrainer from the opening to the closed end thereof, wherein a distal end of the slot rear adjuster is adapted to cover the slot of the restrainer;
wherein the slot front adjuster, if present, is to be inserted into the tunnel with the adjusting slot thereof being right below the slot of the restrainer; the slot rear adjuster, if present, is to be inserted into the tunnel with the distal end of the slot rear adjuster being below the adjusting slot of the slot front adjuster, if present, and below the slot of the restrainer; and the cutting wire is to be inserted into the tunnel of the restrainer with the cutting wire being below the slot rear adjuster, if present, or below the slot front adjuster, if present.

16. The wire cutter of claim 1 wherein the cutting wire is a steel wire, a titanium or titanium alloy wire having a diameter or a width of 0.3 mm to 2.0 mm.

17. The wire cutter of claim 1 wherein the cutting wire is a steel wire, a titanium or titanium alloy wire having a diameter or a width of 0.4 mm to 1.5 mm.

18. A wire cutter comprising a restrainer and a cutting wire, wherein the restrainer comprises an opening at a proximal end thereof, a closed end opposite to the proximal end, a tunnel inside the restrainer and from the opening till the closed end, and a slot parallel to the tunnel and forming a passage from the tunnel to an outside of the restrainer; and said cutting wire adapted to be received in the tunnel, wherein said cutting wire has a distal end and a holding segment away from the distal end, wherein the holding segment is able to be driven to move in the tunnel toward the closed end of the restrainer while the distal end of the cutting wire being stopped directly or indirectly by the closed end of the restrainer, so that a portion of the cutting wire will protrude from the slot to the outside of the restrainer, when the holding segment of the cutting wire is driven to move toward the closed end of the restrainer,
wherein the wire cutter further comprises an advancing means for driving the holding segment of the cutting wire to move toward the closed end of the restrainer and to move away from the closed end after being driven to move toward the closed end of the restrainer, so that a greater portion of the cutting wire will protrude from the slot to the outside of the restrainer as the holding segment of the cutting wire is driven to move closer to the closed end of the restrainer, wherein said advancing means comprises a first wire holder holding the distal end of the cutting wire; a second wire holder holding the holding segment of the cutting wire; a central rod; a compression spring; threads formed in the opening of the tunnel of the restrainer; and a threaded stud having an axial mounting hole at one end thereof, and a handle at another end thereof, wherein the central rod is received in the tunnel of the restrainer with one end thereof being stopped by the closed end of the restrainer and another end thereof protruding from the opening of the restrainer, the first wire holder is slidably received on the central rod with one end of being stopped by the closed end of the restrainer, the compression spring is slidably received on the central rod with one end of being stopped by another end of the first wire holder, the second wire holder is slidably received on the central rod with one end thereof being stopped by another end of the compression spring, and the threaded stud is threadedly received in the opening of the restrainer with the protruding end of the central rod being received in the mounting hole of the threaded stud by rotating the handle of the threaded stud in relative to the restrainer, wherein the second wire holder will be pressed by the threaded stud and moved toward the closed end of the restrainer as the rotation of the handle of the threaded stud is continued, so that the compression spring is compressed by the second wire holder and the first wire holder, and thus the cutting wire is pressed by the second wire holder and protrudes from the slot to the outside of the restrainer.

19. A wire cutter comprising a restrainer and a cutting wire, wherein the restrainer comprises an opening at a proximal end thereof, a closed end opposite to the proximal end, a tunnel inside the restrainer and from the opening till the closed end, and a slot parallel to the tunnel and forming a passage from the tunnel to an outside of the restrainer; and said cutting wire adapted to be received in the tunnel, wherein said cutting wire has a distal end and a holding segment away from the distal end, wherein the holding segment is able to be driven to move in the tunnel toward the closed end of the restrainer while the distal end of the cutting wire being stopped directly or indirectly by the closed end of the restrainer, so that a portion of the cutting wire will protrude from the slot to the outside of the restrainer, when the holding segment of the cutting wire is driven to move toward the closed end of the restrainer, wherein the wire cutter further comprises an advancing means for driving the holding segment of the cutting wire to move toward the closed end of the restrainer and to move away from the closed end after being driven to move toward the closed end of the restrainer, so that a greater portion of the cutting wire will protrude from the slot to the outside of the restrainer as the holding segment of the cutting wire is driven to move closer to the closed end of the restrainer, wherein said advancing means comprises a first wire holder holding the distal end of the cutting wire; a second wire holder holding the holding segment of the cutting wire; a central rod; a compression spring; a clutch rod having an axial mounting hole at one end thereof, and a pushing end at another end thereof, and a control tubular element, wherein the central rod is received in the tunnel of the restrainer with one end thereof being stopped by the closed end of the restrainer, the first wire holder is slidably received on the central rod with one end of being stopped by the closed end of the restrainer, the compression spring is slidably received on the central rod with one end of being stopped by another end of the first wire holder, the second wire holder is slidably received on the central rod with one end thereof being stopped by another end of the compression spring, the clutch rod is inserted into the tunnel of the restrainer via the opening of the restrainer with the mounting hole of the clutch rod accommodating another end of the central rod and the pushing end protruding from the opening of the restrainer, and the control tubular element is connected to the opening of the restrainer with the pushing end of the clutch rod protruding from the control tubular element, wherein a clutch mechanism is provided on an outer surface of the clutch rod and on the control tubular element, so that the clutch rod is able to be stopped by the control tubular element at various positions in relative to the closed end of the restrainer when the clutch rod is pushed back by the compression spring which has be deformed by pushing the pushing end of the clutch rod toward the closed end of the restrainer, wherein the various positions comprise an advanced position where the compression spring is compressed at a relatively greater extent, so that the cutting wire is pressed by the second wire holder and protrudes from the slot to the outside of the restrainer; and a release position where the compression spring is compressed at a relatively less extent, so that the cutting wire is released from the press by the second wire holder and dives from the slot into the tunnel of the restrainer.

20. A wire cutter comprising a restrainer and a cutting wire, wherein the restrainer comprises an opening at a proximal end thereof, a closed end opposite to the proximal end, a tunnel inside the restrainer and from the opening till the closed end, and a slot parallel to the tunnel and forming a passage from the tunnel to an outside of the restrainer; and said cutting wire adapted to be received in the tunnel, wherein said cutting wire has a distal end and a holding segment away from the distal end, wherein the holding segment is able to be driven to move in the tunnel toward the closed end of the restrainer while the distal end of the cutting wire being stopped directly or indirectly by the closed end of the restrainer, so that a portion of the cutting wire will protrude from the slot to the outside of the restrainer, when the holding segment of the cutting wire is driven to move toward the closed end of the restrainer, wherein the wire cutter further comprises a slot adjustment mechanism comprising a slot front adjuster, a slot rear adjuster, or a combination thereof, wherein the slot front adjuster is a long narrow thin plate suitable to be inserted into the tunnel of the restrainer from the opening to the closed end thereof, wherein a distal end of the slot front adjuster is provided with an adjusting slot corresponding to the slot of the restrainer;

wherein the slot rear adjuster is a long narrow thin plate suitable to be inserted into the tunnel of the restrainer from the opening to the closed end thereof, wherein a distal end of the slot rear adjuster is adapted to cover the slot of the restrainer; and wherein the slot front adjuster, if present, is to be inserted into the tunnel with the adjusting slot thereof being right below the slot of the restrainer; the slot rear adjuster, if present, is to be inserted into the tunnel with the distal end of the slot rear adjuster being below the adjusting slot of the slot front adjuster, if present, and below the slot of the restrainer; and the cutting wire is to be inserted into the tunnel of the restrainer with the cutting wire being below the slot rear adjuster, if present, or below the slot front adjuster, if present.

\* \* \* \* \*